(12) United States Patent
Fernandez Dell'Oca (10) Patent No.: US 9,795,431 B2
(45) Date of Patent: Oct. 24, 2017

(54) LONG-NOSED CRIMP PLIERS FOR USE IN ORTHOPEDICS

(75) Inventor: Alberto A. Fernandez Dell'Oca, Montevideo (UY)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1955 days.

(21) Appl. No.: 12/295,815

(22) PCT Filed: Apr. 20, 2007

(86) PCT No.: PCT/US2007/009740
§ 371 (c)(1),
(2), (4) Date: Nov. 13, 2008

(87) PCT Pub. No.: WO2007/124100
PCT Pub. Date: Nov. 1, 2007

(65) Prior Publication Data
US 2009/0171402 A1  Jul. 2, 2009

Related U.S. Application Data

(60) Provisional application No. 60/793,623, filed on Apr. 21, 2006.

(51) Int. Cl.
*A61B 17/82* (2006.01)
*A61B 17/88* (2006.01)
*A61B 17/84* (2006.01)

(52) U.S. Cl.
CPC .......... *A61B 17/8861* (2013.01); *A61B 17/82* (2013.01); *A61B 17/823* (2013.01); *A61B 17/842* (2013.01); *A61B 17/88* (2013.01); *A61B 17/8869* (2013.01)

(58) Field of Classification Search
CPC .............. A61B 17/82–17/842; A61B 17/8861
See application file for complete search history.

(56) References Cited

U.S. PATENT DOCUMENTS

| | | | |
|---|---|---|---|
| 2,725,632 A | 12/1955 | Rabben | |
| 2,959,858 A | 11/1960 | Deake | |
| 3,791,189 A * | 2/1974 | Lawson | 72/409.16 |
| 4,587,963 A | 5/1986 | Leibinger et al. | |
| 4,889,110 A * | 12/1989 | Galline et al. | 606/916 |
| 4,966,600 A | 10/1990 | Songer et al. | |

(Continued)

FOREIGN PATENT DOCUMENTS

| | | |
|---|---|---|
| JP | S60-34437 | 2/1985 |
| JP | H07-503634 | 4/1995 |

(Continued)

*Primary Examiner* — Yashita Sharma
*Assistant Examiner* — Rebecca Preston
(74) *Attorney, Agent, or Firm* — Fay Kaplun & Marcin, LLP (57) ABSTRACT

Cable and crimp assembly kits for fixing bone fractures include long-nose crimp pliers that have a pair of operating handles and connected opposed long jaws. The long jaws are designed to hold and crush a wire crimp. The jaws are long and narrow enough to be able to insert and crush a crimp through a small incision, such as used by a known wire passer tool, at a deeply located bone without spreading or opening wider the small incision. The long-nosed pliers can be used with a crimp alone or with a crimp and an intermediate part that provisionally holds a tension applied to an associated cable or wire.

8 Claims, 8 Drawing Sheets (56) References Cited

U.S. PATENT DOCUMENTS

| | | | |
|---|---|---|---|
| 4,986,457 A * | 1/1991 | Faris | 223/1 |
| 5,116,340 A | 5/1992 | Songer et al. | |
| 5,395,236 A | 3/1995 | Khouri | |
| 5,536,270 A | 7/1996 | Songer et al. | |
| 5,540,698 A * | 7/1996 | Preissman | 606/103 |
| 5,966,815 A * | 10/1999 | Sheikh | 30/124 |
| 6,383,200 B1 | 5/2002 | Wotton, III | |
| 2004/0267275 A1 * | 12/2004 | Cournoyer et al. | 606/99 |

FOREIGN PATENT DOCUMENTS

| | | |
|---|---|---|
| WO | 93/15680 | 8/1993 |
| WO | 93/15880 | 8/1993 |

\* cited by examiner

LONG-NOSED CRIMP PLIERS FOR USE IN ORTHOPEDICS

FIELD OF THE INVENTION

The invention relates to orthopedics, and more particularly to a method and apparatus for securing surgical cable around bone using a minimally invasive technique.

BACKGROUND OF THE INVENTION

The use of surgical cable and crimp assemblies to reduce bone fractures by joining bone fragments together until the bone heals is a well-known technique. Surgical procedures in and around the vicinity of a bone with closely neighboring nerves, arteries, muscles, ligaments, complicated anatomical structures, and other delicate areas represent a difficult and time consuming task for the surgeon. Preparing the cable and crimp assembly accurately is thus important to (1) minimize stress, trauma, risk, and injury to a patient, (2) lessen the difficulty of the procedure, and (3) allow the surgeon to perform the procedure in as little time as possible. The procedure involves looping cables around the fractured bone and tightening the cables with a tensioning tool. The cables are usually connected by a crimp, which is crushed by pliers. The crushed crimp then retains the desired tension on the cables. An example of such a device is disclosed in U.S. Pat. No. 4,966,600.

To obtain a desired tension on a surgical cable looped around a bone, various known tensioning devices may be used. These devices allow the cable to be tensioned by applying a tensioning tool to one end of the cable while butting the tool against a crimp through which the cable had been threaded. The other end of the cable is typically factory crimped to another hole in the crimp, as disclosed in U.S. Pat. Nos. 5,423,820; 6,077,268; and 6,387,099. The same effect is achieved by devices that use a wire with a beaded end, such as disclosed in U.S. Pat. No. 6,017,347. The bead catches on an end of the crimp and prevents the wire from sliding through and out of the crimp.

Also known is a device that provisionally holds the desired tension on a cable looped around a bone. Pluralities of this well-known device, known as an intermediate part, can be used at one per cable to hold and retain as many cables as needed looped and tensioned around a bone (using a tensioning tool), until the appropriate reduction of the bone fracture is achieved.

Other known tools can be used to pass the wire around the bone. Most require pulling from both ends of the cable, as disclosed in U.S. Pat. Nos. 5,649,927 and 6,017,347. These types of tools typically require significant spreading or enlargement of the incision and can cause muscle trauma. Thus, they are not a satisfactory solution.

To solve this difficulty at least in part, a wire passer tool has been developed. This tool permits insertion of the cable and its looping around the bone with a minimal incision, thus reducing tissue injury.

Accordingly, with the development of this wire passer, a need exists for an improved cable and crimp system that permits tensioning and crimping of the cable using the same minimal incision used by the wire passer, thus avoiding the significant spreading or enlargement of the incision and muscle trauma known before, therefore reducing tissue damage.

SUMMARY OF THE INVENTION

It is an object of the invention to provide a device that permits crimping of a cable looped around a fractured bone using a minimally invasive technique.

It is another object of the invention to provide an easy crimping method that requires less surgical time and causes less tissue damage than known methods, while accomplishing the desired reduction of the bone fracture.

It is a further object of the invention to provide a minimally invasive method of bone reduction that allows insertion of multiple cables and crimps with desired tensions to achieve the desired reduction of the bone fracture.

In accordance with the invention, cable and crimp assembly kits are provided that include one or both preferred embodiments of long-nosed pliers. The long-nosed pliers each have a pair of handles and two connected and opposed long jaws. The long jaws are designed to hold and crush a wire crimp at the tip of the jaws. The jaws are also narrow and long enough to reach deeply located bone through a minimal incision without significantly spreading or widening the incision. Methods of bone reduction using the two preferred embodiments of the long-nosed pliers are also provided.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which.

DETAILED DESCRIPTION OF THE INVENTION

FIGS. 1-4A illustrate a first embodiment of the invention.

Figure 1:
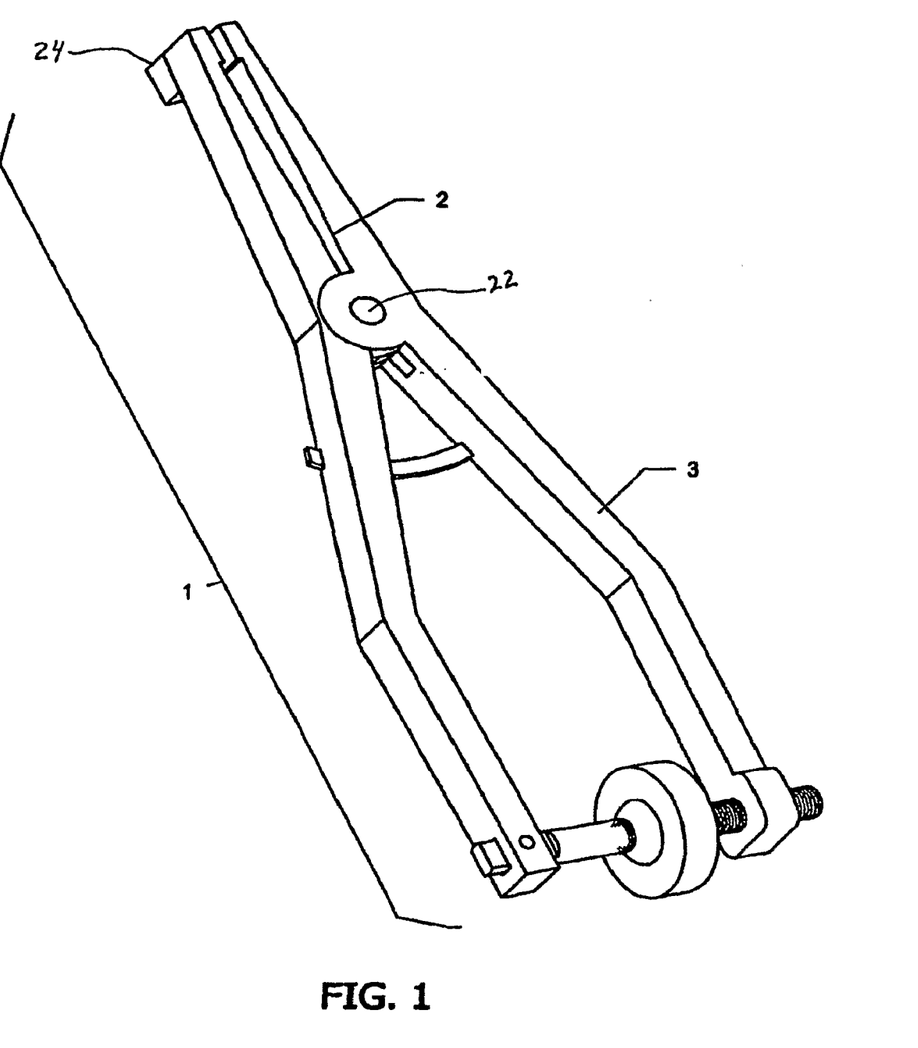
FIG. 1 is a perspective view of long-nosed crimp pliers according to a first embodiment of the invention.
Figure 2:
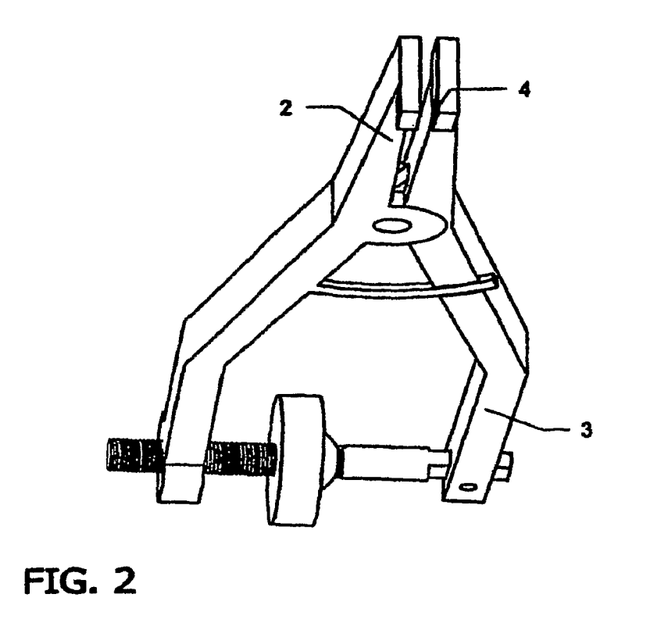
FIG. 2 is another perspective view of the long-nosed crimp pliers according to the first embodiment of the invention.
Figure 2A:
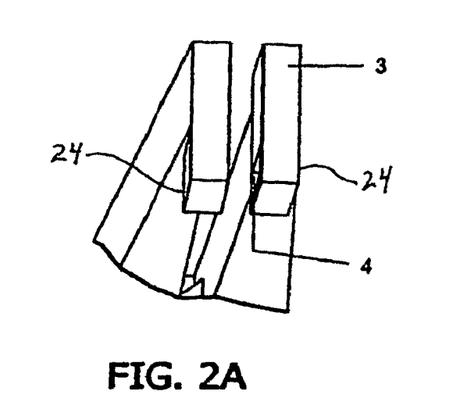
FIG. 2A is an enlarged perspective view of the jaws of the long-nosed crimp pliers of FIGS. 1 and 2.
Figure 3:
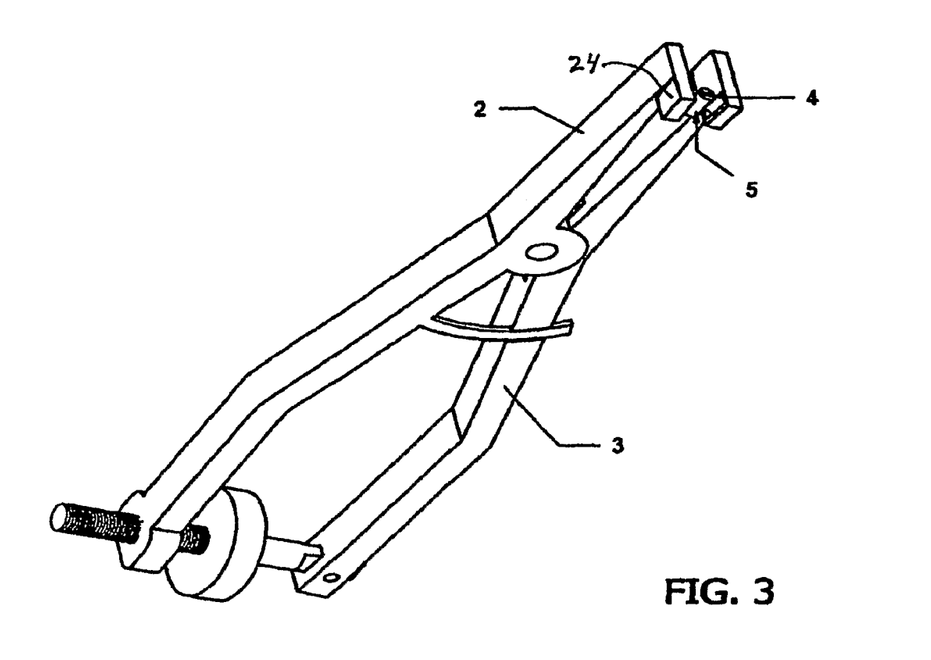
FIG. 3 is a perspective view of the crimp pliers holding a crimp according to the first embodiment of the invention.
Figure 3A:
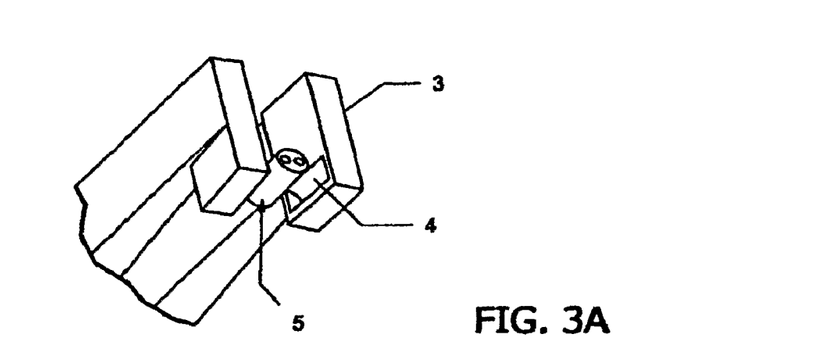
FIG. 3A is an enlarged perspective view of the jaws of the pliers of FIG. 3 holding the crimp.

Long-nosed crimp pliers 1 has a pair of operating handles 3 and connected opposed long jaws 2. Jaws 2 are connected to each other via a hinge mechanism 22. Each jaw 2 is long and narrow and has an extension 24 that extends perpendicularly from the tip of the jaw. Each extension 24 has an internal recess 4 bounded on four sides shaped to accommodate a wire/cable crimp 5. Each extension 24 and recess 4 is positioned opposite the other extension and recess such that jaws 2 are operative to hold and/or crush the crimp there between. A crimp is preferably pre-loaded in recess 4 prior to the crimp's insertion into a patient. This allows pliers 1 to carry crimp 5, as shown in FIGS. 3 and 3A, towards the targeted bone. Jaws 2 are advantageously long and narrow enough to reach a deeply located bone 6 through a minimal incision, and thus deliver crimp 5 to its final position next to the bone. The size of the minimal incision is preferably only that required to permit a wire passer tool to insert a cable through the incision and to loop the cable around a fractured bone.

Figure 4:
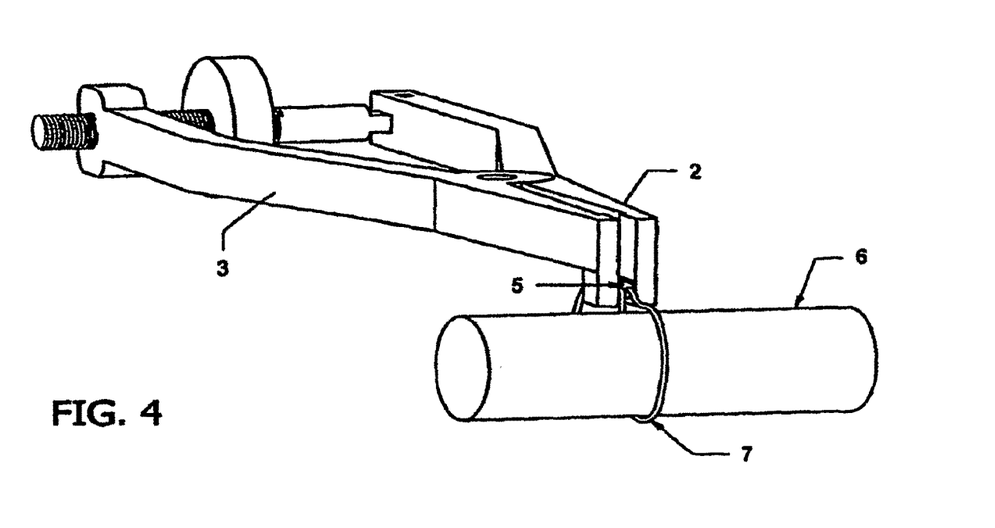
FIG. 4 is a perspective view of the invention showing the long-nosed crimp pliers holding the crimp with a cable passing through the crimp according to the first embodiment.
Figure 4A:
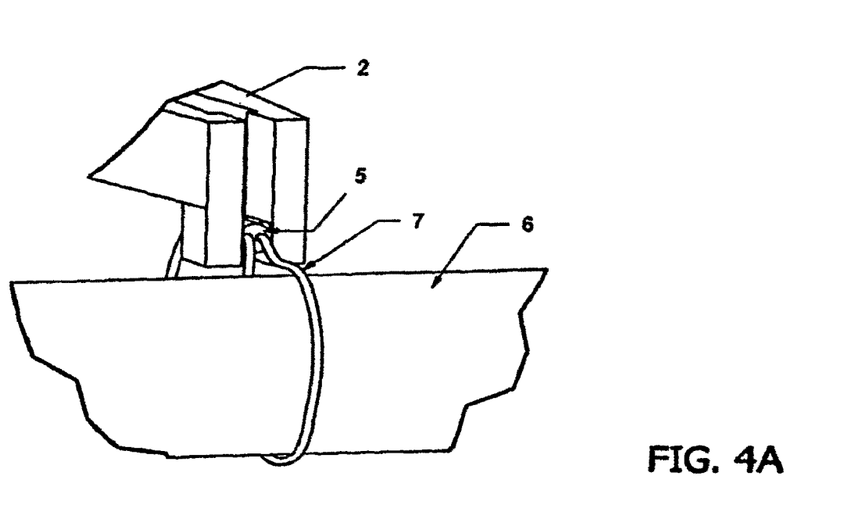
FIG. 4A is an enlarged perspective view of the jaws of the pliers of FIG. 4.

A surgical technique using long-nosed pliers 1 is illustrated in FIGS. 3 to 4A. A flexible cable 7 may first be looped around a fractured bone 6 using, for example, a known wire passer, which advantageously requires only a minimal incision. A wire crimp 5 is loaded in recess 4 of opposed jaws 2 of the pliers, as shown in FIGS. 3 and 3A. Cable 7 may then be passed through crimp 5 in a preferably known manner (alternatively, the cable may be inserted through the crimp before the crimp is loaded in the pliers). The long jaws of pliers 1, with crimp 5 loaded therein and between, are inserted through the minimal incision and moved towards fractured bone 6. Advantageously, because of the sufficient length and narrowness of long jaws 2 (referred to as "long-nosed"), jaws 2 can reach bone 6 without having to spread open or make larger the minimal incision. Thus, pliers 1 can position crimp 5, with flexible cable 7 threaded there through, next to the cortical of fractured bone 6, as shown in FIGS. 4 and 4A. Cable 7 can then be tightened around bone 6 as desired by using, for example, a cable tensioning device. Handles 3 of the pliers are used to crush crimp 5 to retain the tension on the cable. A permanent loop in cable 7 having the desired tightness is now formed around fractured bone 6, with crimp 5 and cable 7 in the desired position with the desired tension. Long jaws 2 can now be opened to release crimp 5. Pliers 1 can then be removed from the patient, leaving crimp 5 and cable 7 in their final positions at fractured bone 6. The remaining portion of cable 7 may now be cut or otherwise dealt with.

Advantageously, the long-nosed pliers of the invention provide surgeons with an easy surgical technique that allows them to properly reduce bone fractures using a cable and crimp system with a minimally invasive technique requiring a short amount of surgical time.

FIGS. 5-8B illustrate a second embodiment of the invention.

Figure 5:
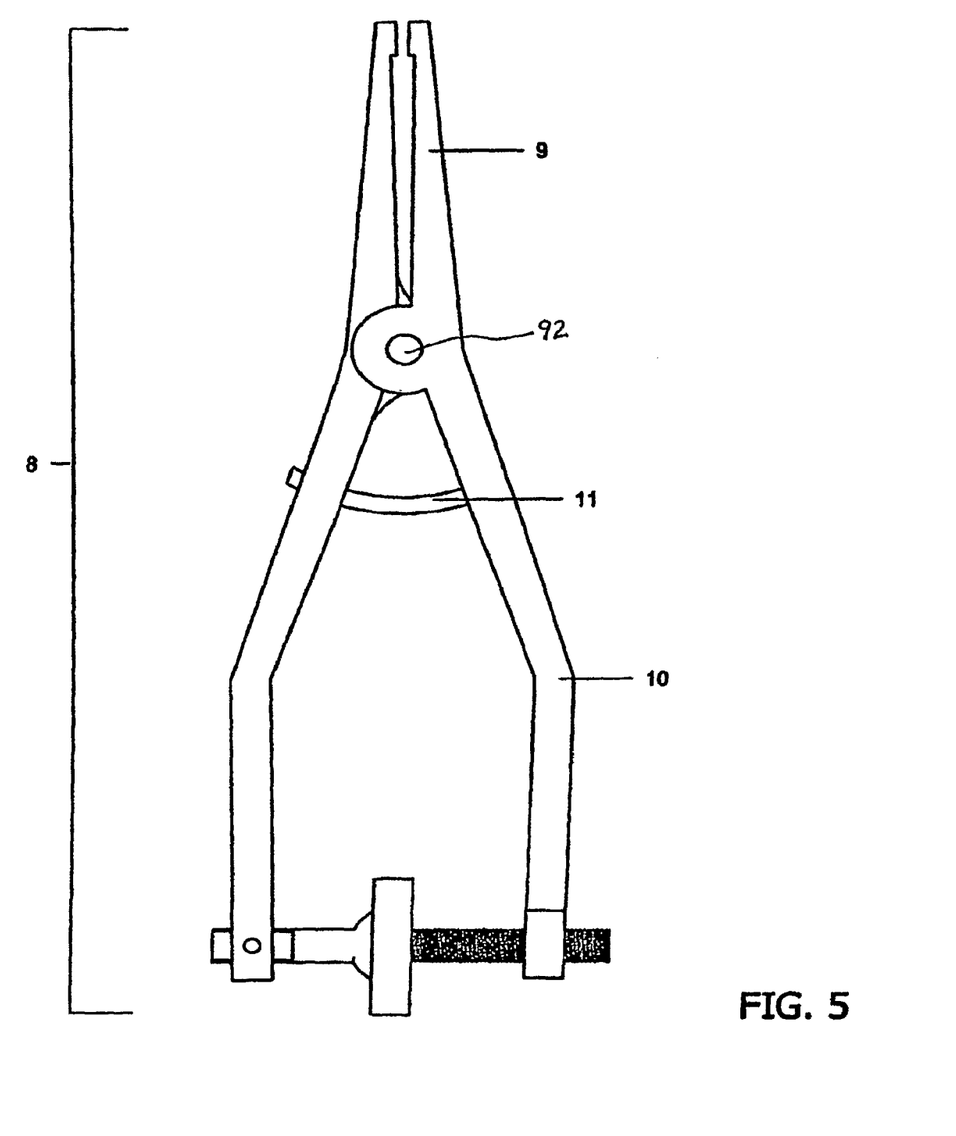
FIG. 5 is a top view of long-nosed crimp pliers according to a second embodiment of the invention.
Figure 6:
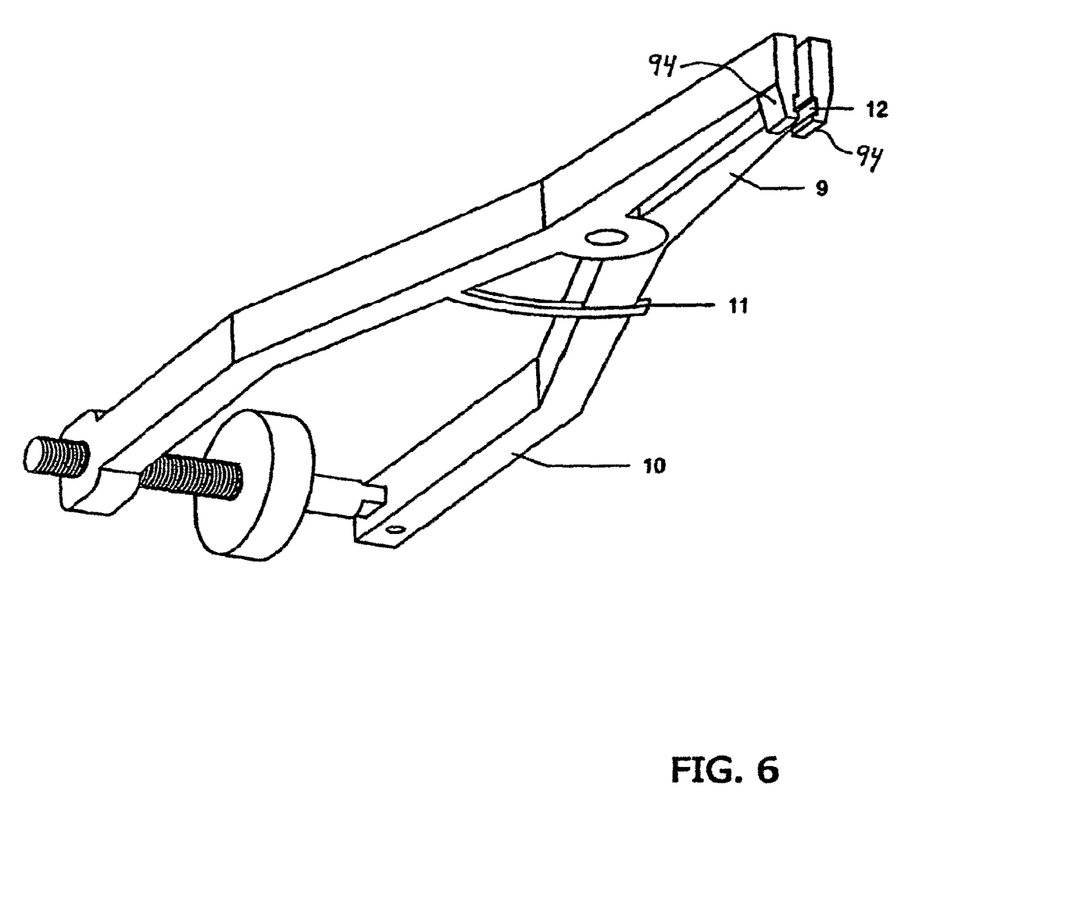
FIG. 6 is a perspective view of the long-nosed crimp pliers of FIG. 5.

Long-nosed pliers 8 have a pair of operating handles 10, a mark 11 attached to and across handles 10, and opposed long jaws 9 connected to handles 10. Jaws 9 are also connected to each other via a hinge mechanism 92. Jaws 9 are advantageously long and narrow enough to permit their deep insertion through a minimal incision up to a fractured bone 6. The size of the minimal incision is preferably only that required to permit a wire passer tool to insert a cable through the incision and to loop the cable around a fractured bone. Each jaw 9 has an extension 94 that extends perpendicularly from the tip of the jaw. Each extension 94 has an internal slot 12 bounded on two parallel sides designed to accommodate a wire/cable crimp 13 and an elongated known intermediate part 14, which is used in surgical procedures to reduce bone fractures. Each extension 94 and slot 12 is positioned opposite the other extension and slot such that jaws 9 are operative to hold and/or crush the crimp there between. Crimp 13 preferably has the same external (cross-sectional) shape and size as intermediate part 14, so that it can form a continuous elongated piece when attached to the intermediate part, as illustrated in FIG. 7A. Intermediate part 14 is a device used to provisionally hold a desired tension applied to cable 7 by means of, for example, a cable tensioner. Intermediate part 14 permits the provisional tightening and loosening of cable 7 until the desired tension and/or bone reduction is achieved. The location of mark 11 on pliers 8 is calibrated to the combined length of intermediate part 14 and an attached crimp 13 such that, after insertion of intermediate part 14 and crimp 13 into an incision, jaws 9 can be moved or slid over intermediate part 14 and crimp 13 until mark 11 reaches rear end 16 of intermediate part 14. This indicates to the surgeon that jaws 9 are now located at crimp 13. The surgeon can now crush crimp 13 with pliers 8 advantageously without having to see crimp 13 between jaws 9.

Figure 7:
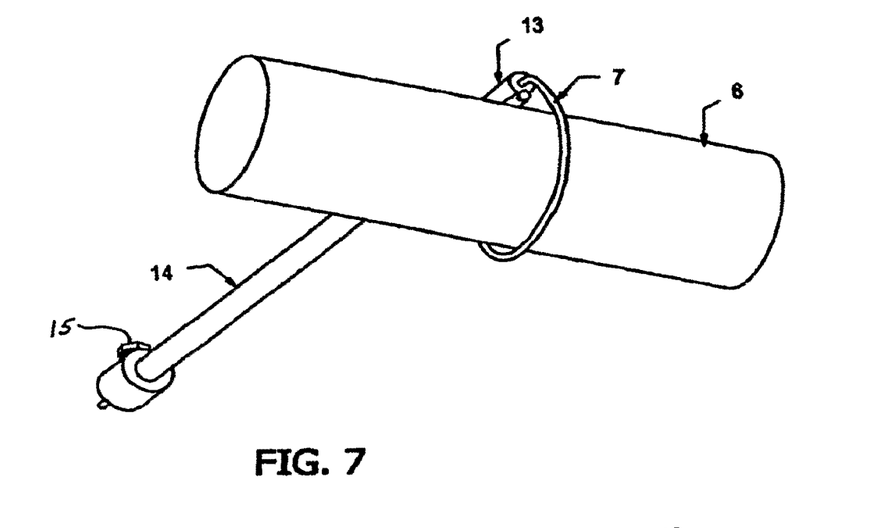
FIG. 7 is a perspective view of an intermediate part and a crimp holding a cable looped around a bone.
Figure 7A:
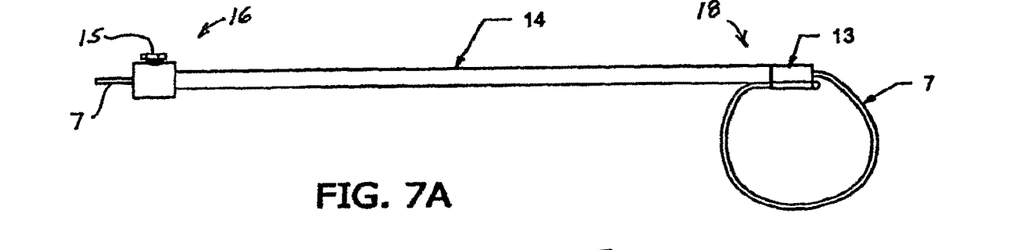
FIG. 7A is a side view of the intermediate part and the crimp holding the cable.
Figure 7B:
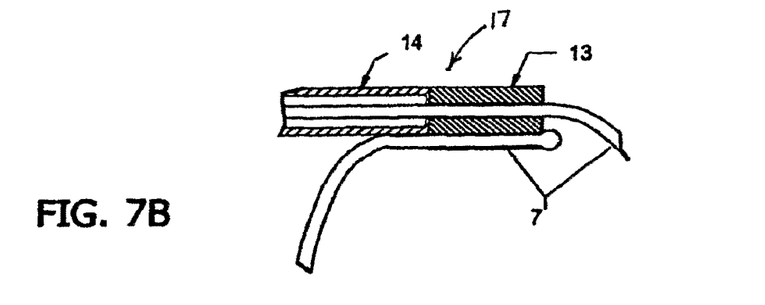
FIG. 7B is an enlarged view of a longitudinal section of the intermediate part and the crimp holding the cable.
Figure 8:
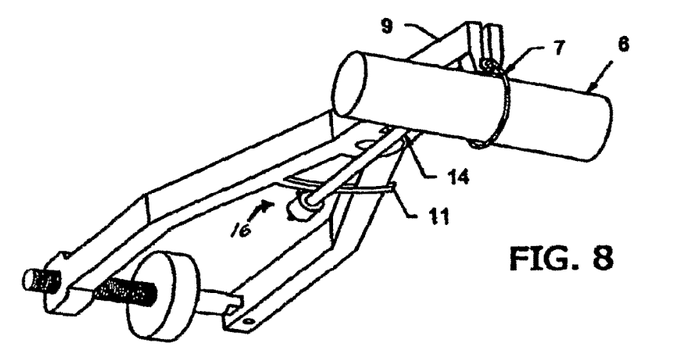
FIG. 8 is a perspective view of the long-nosed crimp pliers holding the crimp attached to the intermediate part during a surgical procedure according to the second embodiment of the invention.
Figures 8A, 8B:
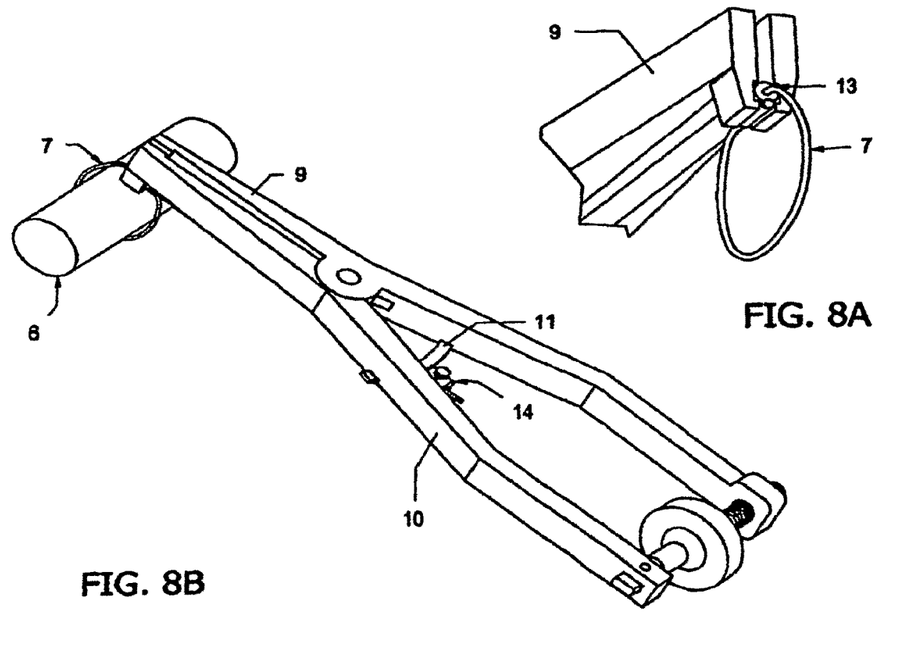
FIG. 8A is an enlarged perspective view of the jaws of the long-nosed crimp pliers holding the crimp attached to the intermediate part during the surgical procedure according to the second embodiment of the invention.
FIG. 8B is another perspective view of the long-nosed crimp pliers holding the crimp attached to the intermediate part during the surgical procedure according to the second embodiment of the invention.

A surgical technique using long-nosed pliers 8 is illustrated in FIGS. 7-8B. A flexible cable 7 may first be looped around a fractured bone 6 using, for example, a known wire passer, which advantageously requires only a minimal incision. Flexible cable 7 is threaded through an opening in crimp 13 in a preferably known manner, and crimp 13 may then be inserted with pliers 8 through the minimal incision and preferably up to bone 6 of a patient. Cable 7 is threaded through intermediate part 14, which may then be deeply introduced through the minimal incision up to crimp 13, such that the front end of intermediate part 14 attaches to the rear end 17 of crimp 13, as shown in FIGS. 7-7B. Alternatively, after cable 7 is passed through crimp 13, cable 7 may then be passed through intermediate part 14, and the front end 18 of intermediate part 14 may be attached to crimp 13. Intermediate part 14 and crimp 13 may then be inserted together through the minimal incision up to bone 6. With crimp 13 located next to bone 6, the rear end 16 of intermediate part 14 remains outside the patient (i.e., outside the minimal incision). Tension is applied to cable 7 by, for example, a cable tensioning device, which may further solidly affix intermediate part 14 to crimp 13. After the desired tension is obtained, intermediate part 14 can be used to provisionally hold that tension at its rear end 16 by tightening set screw 15 down on the cable 7 passing through the intermediate part.

The above steps may be repeated, using as many cables 7, crimps 13, and intermediate parts 14 as necessary to properly reduce the bone fracture. The tension of each cable 7 is provisionally held, and may be adjusted (i.e., tightened or loosened) as needed, by a respective intermediate part 14, until the bone reduction is satisfactory.

After the fracture reduction has been provisionally set, crimp(s) 13 can be crushed by pliers 8 to retain the looped cable(s) 7 surrounding bone 6 with the desired tension. This is done by engaging intermediate part 14 with and between jaws 9 of long-nosed pliers 8. Pliers 8 can then be inserted through the minimal incision used by the wire passer, sliding jaws 9 along intermediate part 14 as pliers 8 advances toward bone 6. Because crimp 13 has the same cross-sectional shape and size as intermediate part 14, jaws 9 continue to slide onto crimp 13 after reaching front end 18 of intermediate part 14 advantageously without needing any additional maneuvers. The long jaws of pliers 8 are deeply introduced into the incision until mark 11 on pliers 8 reaches the rear end 16 of intermediate part 14 (which is located outside the incision and is thus visible to the surgeon), as shown in FIGS. 8 and 8B. Mark 11 indicates that the jaws of pliers 8 are located at the same depth as crimp 13, and thus exactly over the deeply inserted crimp, which is now held between jaws 9, as shown in FIG. 8A. Handles 10 of pliers 8 can now be used to crush crimp 13, deeply located next to bone 6. Crimp 13 and cable 7 are thus retained in the desired position with the desired tension. Pliers 8 can now be opened to release crimp 13 and removed from the patient advantageously without enlarging or spreading open the incision. Thereafter, intermediate part 14 can be removed, and the remaining cable 7 may be cut or otherwise dealt with.

These last steps using long-nosed pliers 8 to crush crimp 13 can be repeated for each cable, crimp, and intermediate part assembly used to reduce the fracture.

Advantageously, pliers 8, intermediate part 14, and crimp 13 allow a surgeon to reduce a bone fracture with multiple crimps and cables using a minimally invasive and easy technique.

Accordingly, the invention includes cable and crimp assembly kits. One kit according to the invention includes pliers 1, at least one crimp 5, and a length of flexible wire or cable 7. Crimp 5 may be of the type that includes a through hole and a second hole with an end of cable 7 factory crimped therein. Another kit according to the invention includes pliers 8, at least one crimp 13, at least one intermediate part 14, and a length of flexible wire or cable 7. Crimp 13 also may be of the type that includes a through hole and a second hole with an end of cable 7 factory crimped therein. And another kit according to the invention includes both pliers 1 and 8, a plurality of both crimps 5 and 13, at least one intermediate part 14, and a length of flexible wire or cable 7.

The invention has been described in connection with the preferred embodiments. However, these embodiments are merely for example, and the invention is not restricted to them. It will be understood by those skilled in the art that other variations and modifications can be easily made within the scope of the invention.

For example, the devices and techniques of the first and second embodiments may be used in non-surgical procedures that require the retaining of a tightened wire or cable around a structure in an enclosure via a small opening in the enclosure. More particularly, for example, a pair of pipes in a wall of a building may need to be tightly wired together, and for aesthetic reasons, can only be done through as small a hole or opening in the wall as possible.

In general, and depending on the circumstances, long-nosed pliers 1 may be used to insert a wire crimp through a small incision-like opening in an enclosure as described above with respect to FIGS. 1-4A. For example, pliers 1 may locate the crimp next to a structure around which a wire or cable has been looped and threaded through the crimp. After the wire or cable is tightened as desired, pliers 1 may be used to crush the crimp, retaining the desired tension on the wire or cable. Handles 3 are then used to release the jaws of pliers 1 from the crimp, and pliers 1 can be removed from the enclosure through the small opening advantageously without enlargement of or spreading wider the opening. The remaining wire may be dealt with as desired.

Alternatively, long-nosed pliers 8 may be used with a crimp and an intermediate part (or similar tool) as described above with respect to FIGS. 5-8A. For example, a flexible wire may first be inserted through the small incision-like opening in the enclosure and looped around the structure. The flexible wire can then be threaded through a hole in a crimp and through the intermediate part while both are located outside the enclosure. The front end of the intermediate part can be attached to the crimp. The intermediate part and crimp may then be inserted into the enclosure through the small opening and up to the structure, with rear end 16 of the intermediate part remaining outside the enclosure. The wire around the structure can now be tightened with a desired tension, and the intermediate part can be used to provisionally hold that tension. Pliers 8 can be used to engage the intermediate part between slots 12 of the jaws and inserted into the enclosure through the small opening advantageously without enlargement of the small opening. As pliers 8 are inserted, jaws 9 slide along the intermediate part until mark 11 on the pliers reaches rear end 16 of the intermediate part. This indicates that jaws 9 now have crimp 13 there between, at which point, pliers 8 can be used to crush crimp 13 to retain the provisionally held tension on the wire. Pliers 8 can then be disengaged from the crushed crimp and removed from the enclosure. The intermediate part may now also be removed from the enclosure, and the remaining wire may be dealt with as desired.

In conclusion, the invention is only intended to be limited by the following claims.

I claim:

1. A surgical cable and crimp assembly kit comprising:
a length of flexible cable;
a crushable wire crimp having at least one hole there through sized to receive the flexible cable there through; and
crimp pliers comprising:
a pair of operating handles; and
a pair of opposed jaws sized and shaped to be inserted through a small incision to a bone about which the cable is to be fixed via the wire crimp, each jaw extending from a respective handle and coupled to the other jaw via a hinge mechanism, an extension extending perpendicularly from the tip of each jaw, each extension including a recess formed therein and being disposed opposite to the other extension, the recess sized and shaped to receive the wire crimp such that the pair of jaws is operative to hold and crush the wire crimp there between, each recess being substantially aligned with a length of a corresponding one of the jaws such that the wire crimp is receivable between the pair of jaws along a longitudinal axis of the crimp pliers.

2. The assembly kit of claim 1 wherein each recess is bounded on four sides and faces the recess in the extension of the opposed jaw.

3. The assembly kit of claim 1 wherein each recess is a slot bounded on two opposite sides and faces the slot in the extension of the opposed jaw.

4. The assembly kit of claim 1 wherein the flexible cable is surgical cable suitable for use in bone fracture surgery.

5. The assembly kit of claim 1 further comprising an intermediate part having a front end, a rear end, and a same cross-sectional size and shape as the wire crimp.

6. The assembly kit of claim 5 wherein the pliers further comprise a mark attached to and across the operating handles, the location of the mark across the operating handles calibrated to the combined length of the intermediate part and the wire crimp to indicate that the jaws are located at the wire crimp when the rear end of the intermediate part aligns with the mark.

7. The assembly kit of claim 5 wherein the intermediate part has a set screw at the rear end for provisionally holding the cable.

8. The assembly kit of claim 5 wherein the front end of the intermediate part is configured to attach to an end of the wire crimp.

* * * * *